(12) United States Patent
Ikeya

(10) Patent No.: US 10,054,578 B2
(45) Date of Patent: Aug. 21, 2018

(54) FUEL PROPERTY SENSOR

(71) Applicant: Aisan Kogyo Kabushiki Kaisha, Obu-shi (JP)

(72) Inventor: Masaki Ikeya, Obu (JP)

(73) Assignee: AISAN KOGYO KABUSHIKI KAISHA, Abu-shi (JP)

( * ) Notice: Subject to any disclaimer, the term of this patent is extended or adjusted under 35 U.S.C. 154(b) by 362 days.

(21) Appl. No.: 14/877,338

(22) Filed: Oct. 7, 2015

(65) Prior Publication Data

US 2016/0097758 A1 Apr. 7, 2016

(30) Foreign Application Priority Data

Oct. 7, 2014 (JP) ................................. 2014-206561

(51) Int. Cl.
*G01N 33/00* (2006.01)
*G01N 33/28* (2006.01)
*F01M 11/10* (2006.01)

(52) U.S. Cl.
CPC ....... *G01N 33/2847* (2013.01); *G01N 33/287* (2013.01); *G01N 33/2888* (2013.01); *F01M 2011/146* (2013.01); *F01M 2011/1406* (2013.01)

(58) Field of Classification Search
CPC .......... G01N 33/2847; G01N 33/2835; G01N 33/287; G01N 33/2876; G01N 33/2888; G01N 27/06; G01N 27/07; G01N 27/121; B60R 16/0234; F01M 2011/14; F01M 2011/1406; F01M 2011/146; F16N 29/04
See application file for complete search history.

(56) References Cited

U.S. PATENT DOCUMENTS

| 4,675,662 A | 6/1987 | Kondo |
| 4,792,791 A | 12/1988 | Cipris |
| 5,331,287 A | 7/1994 | Yamagishi |

(Continued)

FOREIGN PATENT DOCUMENTS

| JP | S61-041955 A | 2/1986 |
| JP | H2-124541 U | 10/1990 |

(Continued)

OTHER PUBLICATIONS

Japanese Office Action for JP Pat. App. No. 2014-206561 dated Dec. 26, 2017.

*Primary Examiner* — Blake A Tankersley
(74) *Attorney, Agent, or Firm* — Shumaker, Loop & Kendrick, LLP

(57) ABSTRACT

A fuel property sensor including a substrate, a first lead wire, a second lead wire, a wiring member, and a determiner. The substrate is disposed in such a position as to be in contact with the fuel. The first lead wire is connected to the substrate. The second lead wire is connected to the substrate. The second lead wire is spaced from the first lead wire. The wiring member is provided on the substrate. The wiring member connects the first lead wire and the second lead wire. The wiring member is configured to electrically disconnect the first lead wire and the second lead wire from each other by reaction with impurities contained in the fuel. The determiner is configured to determine whether the first lead wire and the second lead wire are electrically connected.

7 Claims, 18 Drawing Sheets

(56) References Cited

U.S. PATENT DOCUMENTS

2003/0046985 A1\* 3/2003 Schoess ................ B01D 27/08
  73/53.05
2004/0250606 A1\* 12/2004 Buttgenbach ...... G01N 33/2888
  73/61.49
2012/0206253 A1 8/2012 Taniguchi

FOREIGN PATENT DOCUMENTS

| JP | H6-160319 A | 6/1994 |
| JP | H07-33037 Y | 7/1995 |
| JP | 2004-286630 A | 10/2004 |
| JP | 2011-226843 A | 11/2011 |
| JP | 2012-145330 A | 8/2012 |
| JP | 2013-205211 | 7/2013 |
| JP | 2013-134111 | 8/2013 |
| WO | 2011-052052 A1 | 5/2011 |

\* cited by examiner

FIG. 23
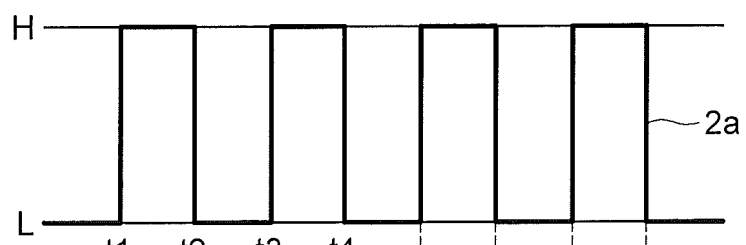
(A)
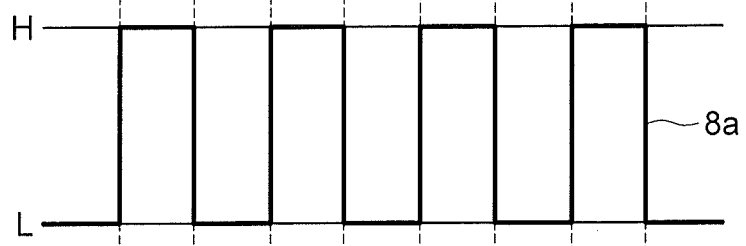
(B)
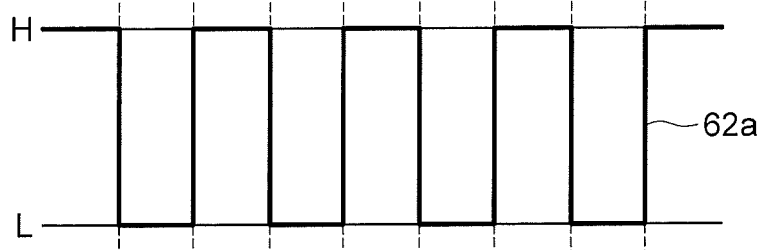
(C)
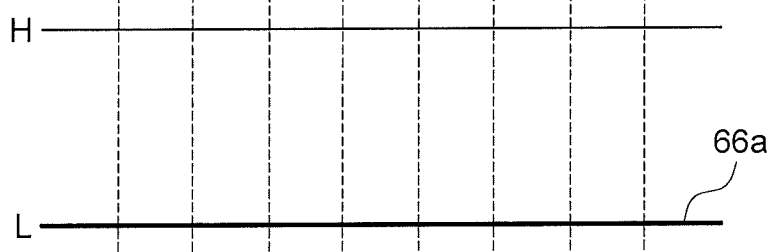
(D)
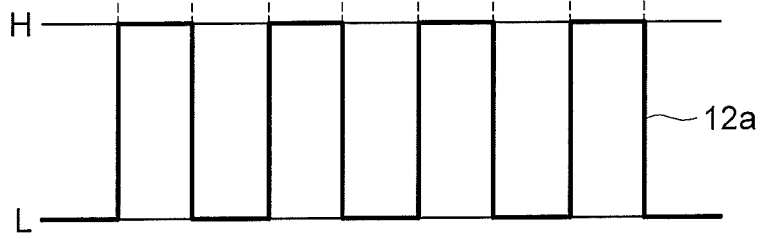
(E)

FIG. 24
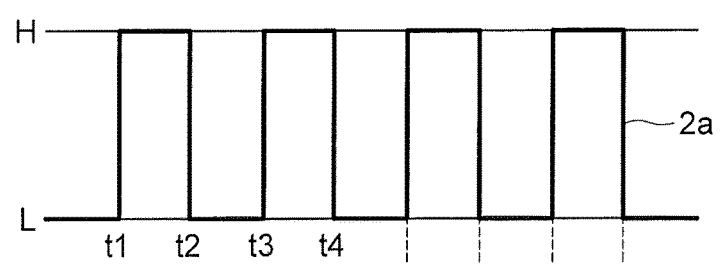
(A)
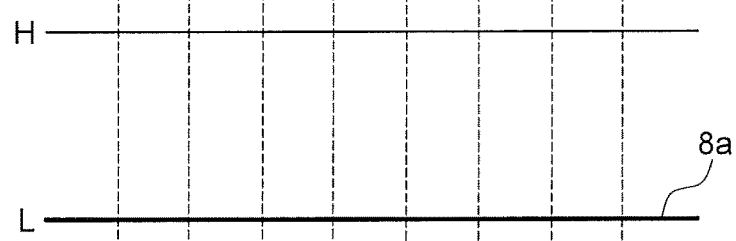
(B)
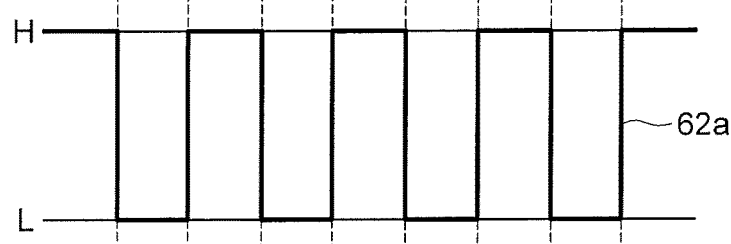
(C)
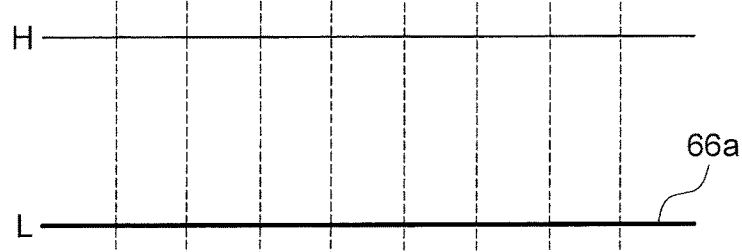
(D)
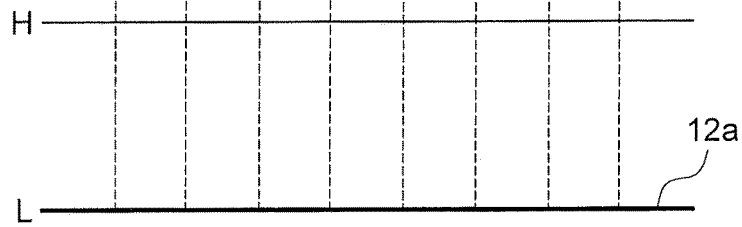
(E)

FUEL PROPERTY SENSOR

CROSS-REFERENCE TO RELATED APPLICATION

This application claims priority from Japanese Patent Application No. 2014-206561 filed Oct. 7, 2014, the contents of which are hereby incorporated by reference into the present application.

TECHNICAL FIELD

The present specification discloses a technique relating to a fuel property sensor configured to detect a property of fuel.

BACKGROUND ART

Japanese Patent Application Publication No. 2011-226843 discloses a sensor for detecting whether there is oxidation degradation of fuel in a fuel tank. Japanese Patent Application Publication No. 2011-226843 is hereinafter referred to as "Patent Document 1". The sensor of Patent Document 1 includes a mesh protecting member, an ion-exchange material disposed in the protecting member, and an electrode pair disposed in the protecting member. The ion-exchange material has low electrical conductivity and the electrode pair is in contact with the ion-exchange material. In the absence of water in the fuel tank, the sensor of Patent Document 1 separates the ion-exchange material and the fuel from each other by using the protective member. Oxidization of the fuel by water in the fuel tank causes a water-soluble oxide to move from outside of the protective member to inside of the protective member. The movement of the oxide to the inside of the protective member leads to formation of a battery by the oxide and the electrode pair. The sensor of Patent Document 1 detects degradation of the fuel by connecting a voltmeter to the electrode pair and detecting the formation of the battery inside of the protecting member.

SUMMARY OF THE INVENTION

The sensor of Patent Document 1 detects degradation of the fuel when a water-soluble oxide has been generated by water having entered the fuel tank. As such, the sensor of Patent Document 1 cannot detect a substance that is hardly soluble in water, impurities contained in fuel per se, or the like. For example, in order to detect a substance that is hardly soluble in water, it is necessary to use a sensor that is different from the sensor of Patent Document 1. The sensor of Patent Document 1 can only detect a property of fuel in a limited way, and is therefore low in versatility. It is an object of the present specification to provide a highly-versatile fuel property sensor.

A fuel property sensor disclosed herein is configured to detect a property of fuel used in an engine. The fuel property sensor comprises a substrate, a first lead wire, a second lead wire, a wiring member, and a determiner. The substrate is disposed in such a position as to be in contact with the fuel. The first lead wire is connected to the substrate. The second lead wire is connected to the substrate, and is spaced from the first lead wire. The wiring member is provided on the substrate, and connects the first lead wire and the second lead wire. Further, the wiring member is configured to electrically disconnect the first lead wire and the second lead wire from each other by reaction with impurities contained in the fuel. The determiner is configured to determine whether the first lead wire and the second lead wire are electrically connected.

The above fuel property sensor is configured such that in a case where the fuel is in a normal state, the first lead wire and the second lead wire are electrically connected by the wiring member. However, in a presence of impurities in the fuel, the wiring member reacts with the impurities to cause the first lead wire and the second lead wire to be electrically disconnected from each other. The determiner determines whether the first lead wire and the second lead wire are electrically connected to each other or electrically disconnected from each other. Selection of a material of which the wiring member is made allows the fuel property sensor to detect a presence of impurities contained in the fuel, even in a case where the impurities are impurities that are hardly soluble in water (e.g. sulfides). The fuel property sensor is simpler and more versatile than a conventional fuel property sensor.

BRIEF DESCRIPTION OF THE DRAWINGS

These and other features, aspects and advantages of the present invention are better understood when the following detailed description of the invention is read with reference to the accompanying drawings, in which:

FIG. 23 is a diagram explaining how the fuel property sensor according to the third embodiment operates;

FIG. 24 is a diagram explaining how the fuel property sensor according to the third embodiment operates;

DESCRIPTION OF THE EMBODIMENTS

Figure 1:
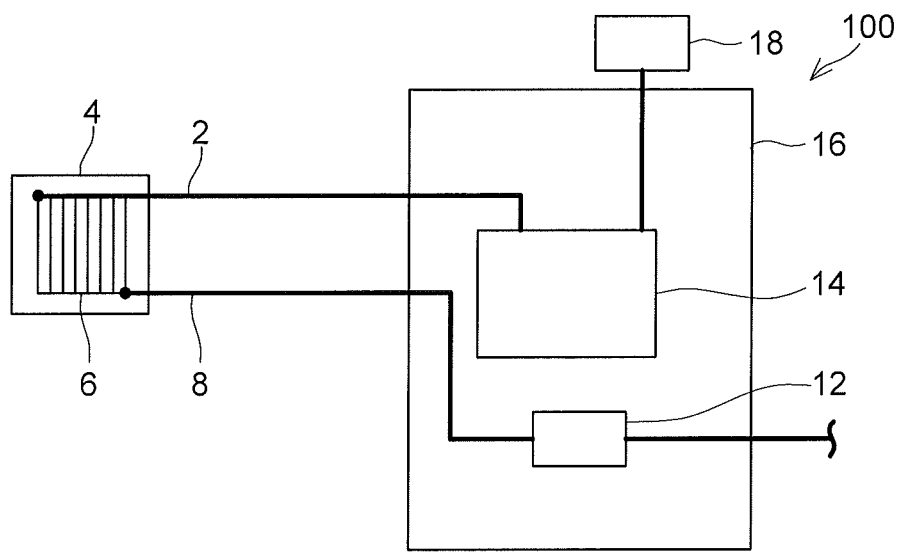
FIG. 1 is a schematic view of a fuel property sensor according to a first embodiment.

The following describes some of the technical features of a fuel property sensor disclosed herein. It should be noted that the matters described below each independently have technical utility.

A fuel property sensor disclosed herein is configured to detect a property of fuel used in an engine. Specifically, the fuel property sensor is disposed in a fuel tank of an automobile and is configured to detect impurities and water contained in the fuel and a product generated by degradation of the fuel. An example of the fuel is gasoline. An example of the impurities contained in the fuel (gasoline) is sulfur (sulfides).

The fuel property sensor disclosed herein may include a substrate, a first lead wire, a second lead wire, a wiring member, and a determiner. The substrate may be insulative. The substrate may be made of a material that does not react with the fuel. The substrate may be disposed in such a position as to be in contact with the fuel, e.g. in the fuel tank, in a subtank, and/or in a fuel passage through which the fuel tank and the subtank communicate with each other. The first lead wire and the second lead wire may be connected to the substrate. The first lead wire may be connected to a signal outputting unit. The second lead wire may be spaced from the first lead wire. That is, the first lead wire and the second lead wire may not need to be directly connected to each other.

The wiring member may be provided on the substrate. The wiring member may connect the first lead wire and the second lead wire. The wiring member may be made of a material that has electrical conductivity. The first lead wire and the second lead wire may be electrically connected by the wiring member. Further, the wiring member may have a film shape. The wiring may be configured of a conductive material adhering on a surface of the substrate. For example, the wiring member may be configured of conductive ink applied on the surface of the substrate. Alternatively, the wiring member may be configured of a plated predetermined portion in the surface of the substrate.

The wiring member may connect the first lead wire and the second lead wire only. The wiring member may be provided over an entire area between the first lead wire and the second lead wire. Alternatively, non-wiring regions in any of which the wiring member is not provided may be provided between the first lead wire and the second lead wire, as long as the wiring member connects the first lead wire and the second lead wire. The non-wiring regions correspond to a portion of the surface of the substrate on which the wiring member is not provided. The non-wiring regions may be provided in a repetitive arrangement between the first lead wire and the second lead wire. The non-wiring regions may extend parallel to each other along a direction connecting the first lead wire and the second lead wire (i.e. a direction along which a straight line connecting the first lead wire and the second lead wire extends at a shortest distance; hereinafter referred to as "first direction"). Alternatively, the non-wiring regions may extend along a second direction orthogonal to the first direction. When including the non-wiring regions, the wiring member may have a plurality of conducting paths connecting the first lead wire and the second lead wire. Alternatively, the wiring member may have a single conducting path connecting the first lead wire and the second lead wire.

The wiring member may be made of a material that is corroded by impurities contained in the fuel. That is, the wiring member may be configured to electrically disconnect the first lead wire and the second lead wire from each other by a reaction with impurities contained in the fuel. The material of the wiring member may turn into a non-conductive substance by reaction with the impurities, and/or may become lower in adhesiveness to the substrate by reaction with the impurities, and the wiring member may come off the substrate. Examples of the impurities include sulfur and the like. Examples of the material of the wiring member include silver (Ag), copper (Cu), aluminum (Al), iron (Fe), and the like. Further, the wiring member may turn into an oxide, a chloride, a sulfide, or the like by reaction with the impurities.

The determiner may include a signal outputting unit configured to output a first signal to the first lead wire and a signal receiving unit configured to receive a second signal from the second lead wire. Further, the determiner may be configured to determine, in accordance with the first signal and the second signal, whether the first lead wire and the second lead wire are electrically connected. When the first lead wire and the second lead wire are electrically connected to each other, the first signal outputted from the signal outputting unit is supplied to the second lead wire via the first lead wire and the wiring member. On the other hand, in a case where the first lead wire and the second lead wire are electrically disconnected from each other, the first signal is not supplied to the second lead wire. Due to this, it becomes possible to determine whether the first lead wire and the second lead wire are electrically connected to each other and thus detect whether impurities are contained in the fuel, through analysis of the second signal that is supplied from the second lead wire to the signal receiving unit.

The fuel property sensor disclosed herein may further include a water detector configured to detect water in the fuel. The water detector may be disposed on the substrate, on which the wiring member is provided. That is, the wiring member and the water detector may be provided on the same substrate. The water detector may be a pair of electrodes (i.e. a first electrode and a second electrode) spaced from each other. When the first electrode and the second electrode are electrically connected to each other, the water detector may determine that water is present in a surrounding area of the water detector, whereas when the first electrode and the second electrode are electrically disconnected from each other, the water detector may determine that water is not present in the surrounding area. The first electrode may be connected to the signal outputting unit, and the second electrode may be connected to the signal receiving unit. That is, the same determiner may determine whether the first lead wire and the second lead wire are electrically connected to each other and whether the first electrode and the second electrode are electrically connected to each other. Further, the second electrode may be connected to the second lead wire. That is, a signal outputted from the second electrode may be received by the signal receiving unit, in a state where the signal outputted from the second electrode is combined with the signal (second signal) outputted from the second lead wire.

EMBODIMENTS

First Embodiment

As shown in FIG. 1, a fuel property sensor 100 includes a substrate 4, a first lead wire 2, a second lead wire 8, and a determiner 16. The substrate 4 is disposed in such a position as to be in contact with fuel used in an engine (not illustrated). The first lead wire 2 and the second lead wire 8 are connected to the substrate 4. The first lead wire 2 and the second lead wire 8 are spaced from each other. A wiring member 6 is provided on a front surface of the substrate 4. The wiring member 6 connects the first lead wire 2 and the second lead wire 8. The wiring member 6 has electrical conductivity. Therefore, the first lead wire 2 and the second lead wire 8 are electrically connected to each other. The wiring member 6 will be described in detail later.

The determiner 16 includes a signal outputting unit 14 and a signal receiving unit 12. A power supply 18 is connected to the signal outputting unit 14. The signal outputting unit 14 is configured to supply a signal (current) to the first lead wire 2. Since the first lead wire 2 and the second lead wire 8 are electrically connected by the wiring member 6, the signal receiving unit 12 receives a signal of which waveform is the same as that of the signal outputted by the signal outputting unit 14.

Figure 2:
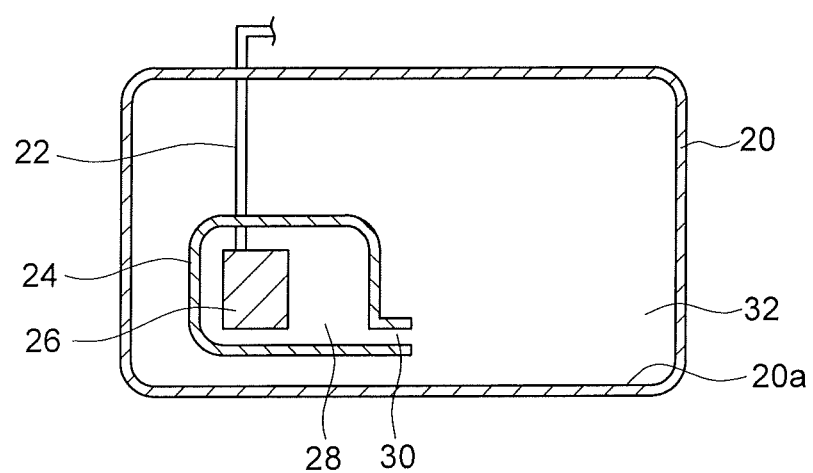
FIG. 2 is a schematic view of a fuel tank.

The following will explain a position in which the fuel property sensor 100 is disposed. FIG. 2 is a schematic view of a fuel tank 20 used in an automobile. A subtank 24 is disposed in the fuel tank 20. Fuel (gasoline) stored in a space 32 in the fuel tank 20 is supplied to the subtank 24 by a pump (not illustrated). The fuel in the space 32 is supplied into the subtank 24 through a fuel passage 30. The fuel in the subtank 24 is supplied to an engine (not illustrated) through a pipe 22 by a pump 26.

The fuel property sensor 100 may be disposed in any position where it can make contact with the fuel in the fuel tank 20. For example, the fuel property sensor 100 may be disposed in the space 32 in which the fuel is stored, in the fuel passage 30, and in a space 28 in the subtank 24. In a case where the fuel property sensor 100 is disposed in the space 32, it may be disposed in vicinity of a bottom face 20a. Alternatively, it is preferable that the fuel property sensor 100 be disposed in a position 3 to 20 mm above the bottom face 20a. This prevents the wiring member 6 from being affected by separated water or the like having accumulated on the bottom face 20a, thus allowing the wiring member 6 to more surely make contact with the fuel.

The wiring member 6 is described with reference to FIGS. 3 to 5. The wiring member 6 is configured of a conductive material (copper or a copper compound) adhering to the front surface of the substrate 4. The wiring member 6 includes a plurality of conducting paths 6a. Each of the conducting paths 6a is in contact with the first lead wire 2 and the second lead wire 8. The conducting paths 6a are placed at intervals from each other. Therefore, non-wiring regions 6b are provided between each of the conducting paths 6b, and the wiring member is not provided in any of the non-wiring regions 6b. Since the conducting paths 6a are placed at intervals from each other, the non-wiring regions 6b are in a repetitive arrangement between the first lead wire 2 and the second lead wire 8.

The material (copper) of the wiring member 6 highly reactive with sulfur (S). Therefore, if sulfur is contained in the fuel (i.e. if the fuel is of poor quality), copper reacts with sulfur (i.e. the wiring member 6 is corroded by sulfur). If the wiring member 6 is corroded by sulfur, the conducting paths 6a lose their electrical conductivity, with a result that the first lead wire 2 and the second lead wire 8 become electrically disconnected from each other. Alternatively, if the wiring member 6 is corroded by sulfur, the conducting paths 6a come off the substrate 4, with the result that the first lead wire 2 and the second lead wire 8 become electrically disconnected from each other.

Figure 4:
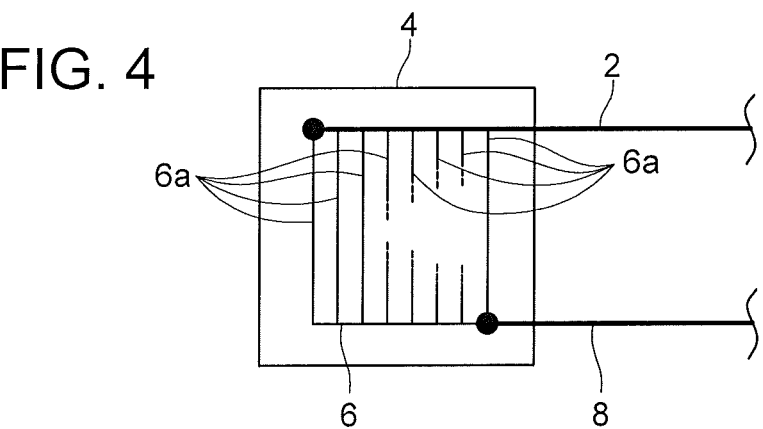
FIG. 4 shows a state in which the wiring member has corroded.
Figure 5:
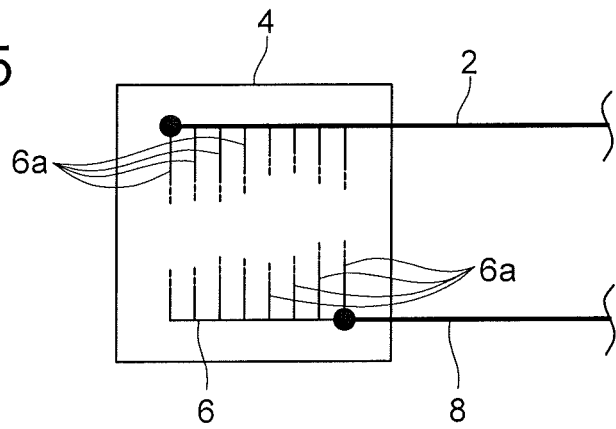
FIG. 5 shows a state in which the corrosion of the wiring member has developed further than in FIG. 4.

FIG. 4 shows a state in which a portion of the wiring member 6 has been corroded by sulfur. Some of the conducting paths 6a in a central portion of the wiring member 6 have been corroded by sulfur. However, some of the conducting paths 6a at ends of the wiring member 6 have not been corroded. Therefore, in the state shown in FIG. 4, the first lead wire 2 and the second lead wire 8 are electrically connected to each other. When, as shown in FIG. 5, the corrosion of the wiring member 6 develops and all of the conducting paths 6a have corroded, the first lead wire 2 and the second lead wire 8 become electrically disconnected from each other. By being provided with the wiring member 6, which is corroded by sulfur, between the first lead wire 2 and the second lead wire 8, the fuel property sensor 100 detects whether or not the fuel is of good quality.

Figure 6:
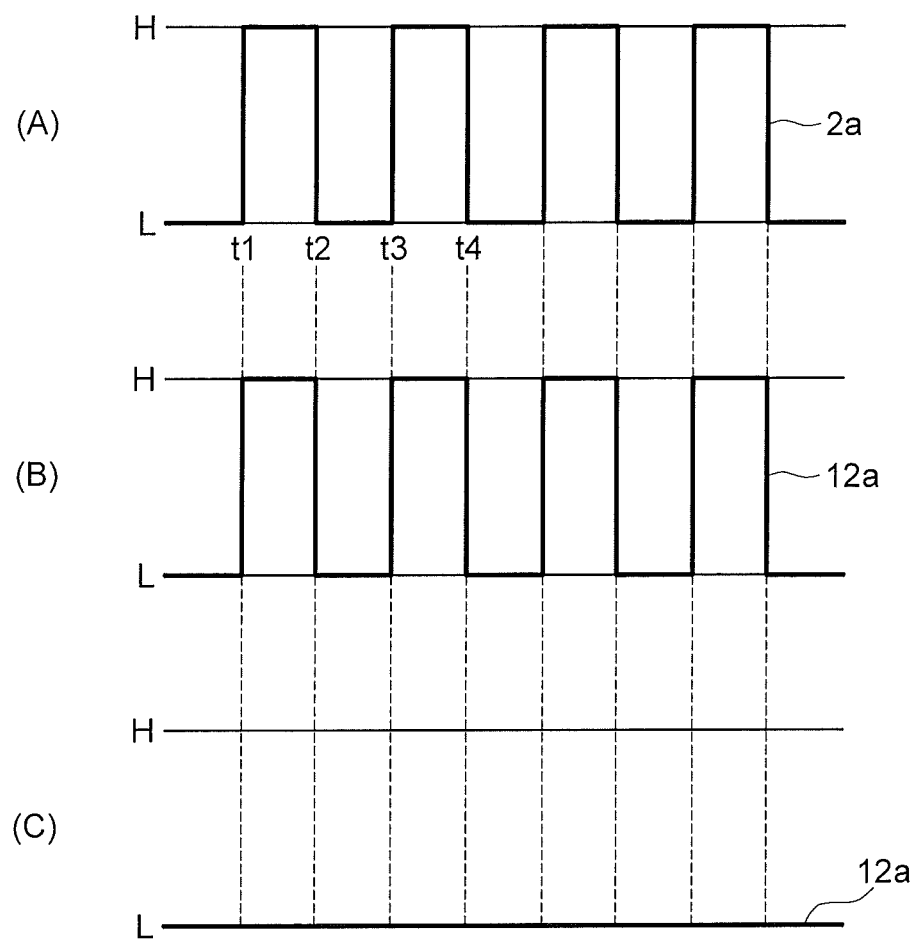
FIG. 6 is a diagram explaining how the fuel property sensor according to the first embodiment operates.

Next, how the fuel property sensor 100 operates is described with reference to FIG. 6. A waveform (A) temporally shows a signal (current) 2a that is outputted from the signal outputting unit 14 to the first lead wire 2. The signal 2a rises to a High state at a timing t1, falls to a Low state at a timing t2, rises to the High state at a timing t3, and falls to the Low state at a timing t4. The signal 2a repeats such changes in state.

Figure 3:
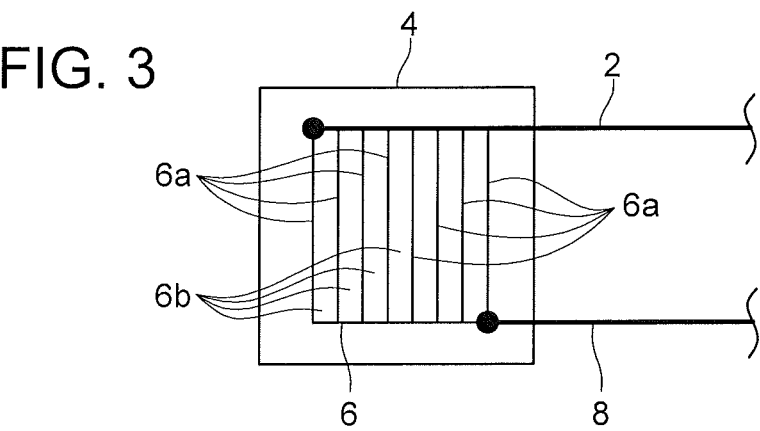
FIG. 3 is a diagram explaining a shape of a wiring member.

A waveform (B) temporally shows a signal 12a as received by the signal receiving unit 12 when the first lead wire 2 and the second lead wire 8 are electrically connected to each other (i.e. the state shown in FIG. 3 or 4). As shown in FIG. 6, the waveform of the signal 2a and the waveform of the signal 12a are identical to each other. A waveform (C) temporally shows the signal 12a as received by the signal receiving unit 12 when the first lead wire 2 and the second lead wire 8 are electrically disconnected from each other (i.e. the state shown in FIG. 5). In other words, the waveform (C) indicates that the signal receiving unit 12 is not receiving a signal. The waveform (B) and the waveform (C) are different from each other. The difference between the waveforms of the signal that is received by the signal receiving unit 12 makes it possible to detect whether the wiring member 6 connects the first lead wire 2 and the second lead wire 8. That is, an analysis of the waveforms of the signal that is received by the signal receiving unit 12 makes it possible to detect whether sulfur is contained in the fuel.

The wiring member 6 may be made of silver instead of copper. Further, when the wiring member 6 is made of copper and/or silver, it is possible to detect not only whether sulfur (sulfides) is contained in the fuel, but also whether oxides and chlorine (chlorides) are contained in the fuel.

Figure 7:
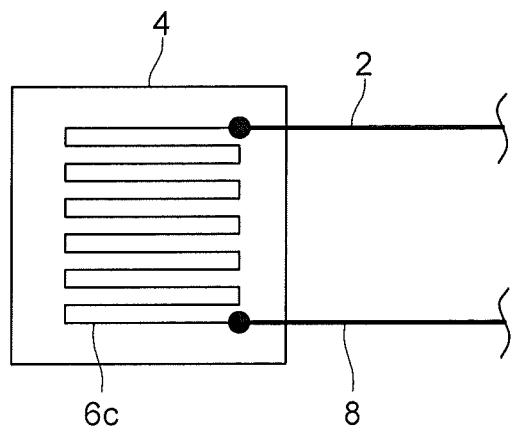
FIG. 7 shows a modification of the wiring member.

Modifications of the wiring member are described with reference to FIGS. 7 to 11. FIG. 7 shows a wiring member 6c. The wiring member 6c is in a shape of a single line. The wiring member 6c has one end connected to the first lead wire 2 and the other end connected to the second lead wire 8. In other words, the wiring member 6c includes only one conducting path. The wiring member 6c extends forward and backward along a direction in which the first lead wire 2 and the second lead wire 8 extend. Therefore, the wiring member 6c has a length that is longer than a distance between the first lead wire 2 and the second lead wire 8.

Figure 8:
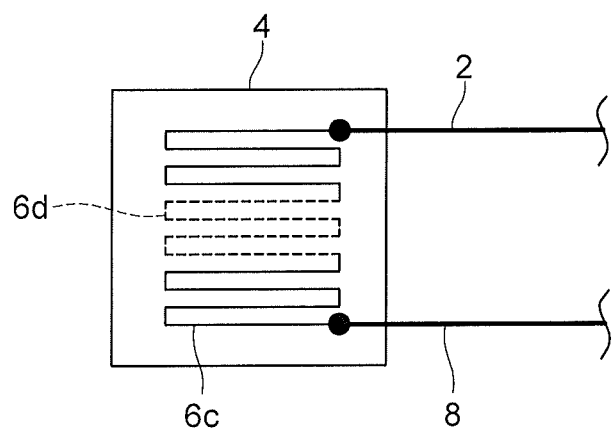
FIG. 8 shows a state in which the wiring member shown in FIG. 7 has corroded.

FIG. 8 shows a state in which a central portion 6d of the wiring member 6c has corroded. Since the wiring member 6c includes only one conducting path, corrosion of even a portion of the wiring member 6c causes the first lead wire 2 and the second lead wire 8 to be electrically disconnected from each other. Use of the wiring member 6c achieves higher sensitivity to impurities such as sulfur than use of the wiring member 6, which has the plurality of conducting paths 6a.

Figure 9:
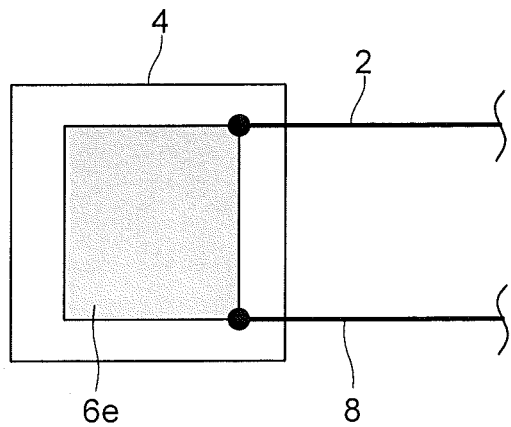
FIG. 9 shows another modification of the wiring member.
Figure 10:
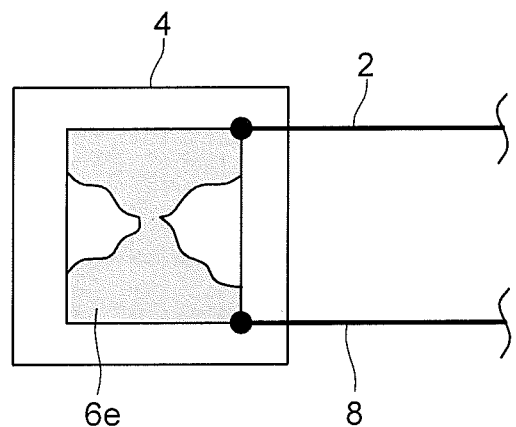
FIG. 10 shows a state in which the wiring member shown in FIG. 9 has corroded.
Figure 11:
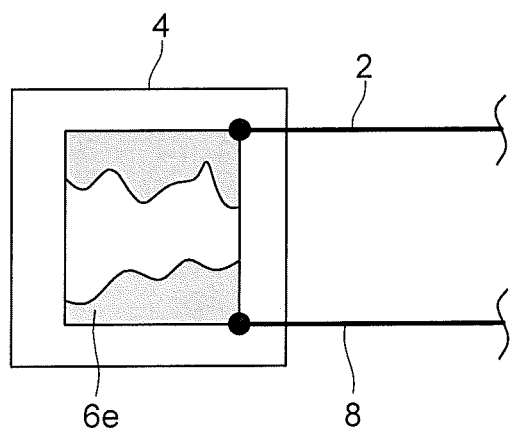
FIG. 11 shows a state in which the corrosion of the wiring member has developed further than in FIG. 9.

FIG. 9 shows a wiring member 6e. The wiring member 6e is shaped in a polygon, and all of an inner part of the polygon comprises a conducting path. More specifically, the wiring member 6e is in a shape of a square, each side of which is equal in length to the distance between the first lead wire 2 and the second lead wire 8. The wiring member 6e has an area that is larger than that of each of the wiring members 6 and 6c. Use of the wiring member 6e makes it possible to prevent the first lead wire 2 and the second lead wire 8 from being broken even if unintended damage is applied to the wiring member 6e. That is, use of the wiring member 6e makes it possible to prevent the fuel from being judged as containing impurities when it actually does not contain impurities. FIG. 10 shows a state in which a portion of the wiring member 6e has corroded. In the state shown in FIG. 10, where the wiring member 6e connects the first lead wire 2 and the second lead wire 8, the first lead wire 2 and the second lead wire 8 are electrically connected to each other. In the state shown in FIG. 11, the wiring member 6e does not connect the first lead wire 2 and the second lead wire 8. When the wiring member 6e enters the state shown in FIG. 11, the fuel is judged as containing impurities.

Figure 12:
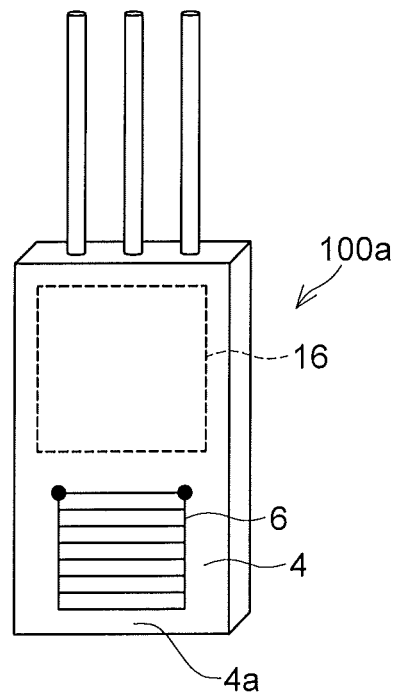
FIG. 12 shows a specific aspect of the fuel property sensor according to the first embodiment.
Figure 13:
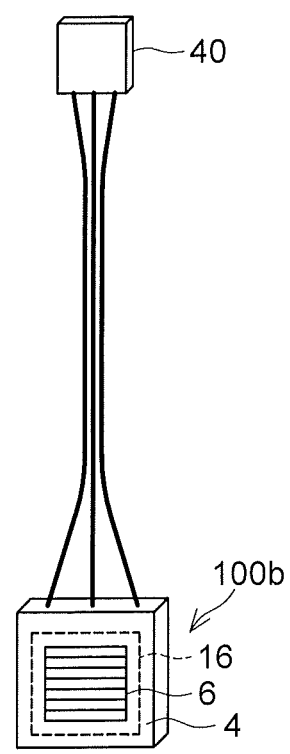
FIG. 13 shows another specific aspect of the fuel property sensor according to the first embodiment.
Figure 14:
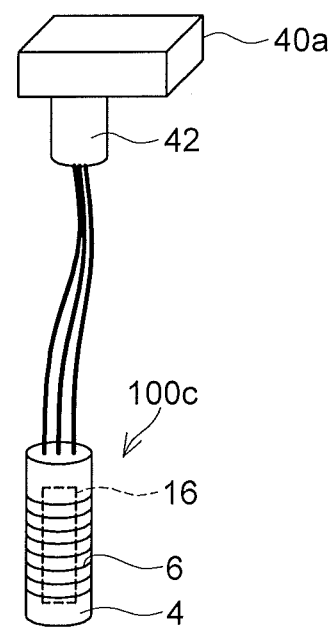
FIG. 14 shows another specific aspect of the fuel property sensor according to the first embodiment.

Specific aspects of the fuel property sensor 100 are described with reference to FIGS. 12 to 14. Fuel property sensors 100a, 100b, and 100c each include an integrated combination of a circuit including the determiner 16 and the wiring member 6. The determiner 16 is sealed with resin so as not to be exposed on the front surface of the substrate 4. Examples of the resin include polyphenylene sulfide resin (PPS), liquid crystal polymer (LCP), polyacetal resin (POM), and the like. The wiring member 6 is exposed on the front surface of the substrate 4. The determiner 16 and the wiring member 6 are connected to each other inside of the substrate 4.

The fuel property sensor 100a has a gap 4a provided between a bottom part of the substrate 4 and the wiring member 6. By adjusting a size of the gap 4a, a distance from the bottom face 20a (see FIG. 2) of the fuel tank 20 to the wiring member 6 can be adjusted within a range of 3 to 20 mm. The fuel property sensor 100b has the wiring member 6 and the determiner 16 that overlap each other when seen in a plan view. The fuel property sensor 100b allows for a reduction in size of the substrate 4. The fuel property sensor 100b includes a connector 40 that allows the fuel property sensor 100b to be connected from inside of the fuel tank 20 to a device (not illustrated) disposed on an upper side of the fuel tank 20. The fuel property sensor 100c includes a columnar substrate 4 and a wiring member 6 provided on an outer circumferential surface of the columnar substrate 4. The fuel property sensor 100c, too, has the wiring member 6 and the determiner 16 that overlap each other, and achieves a reduction in size of the substrate 4. The fuel property sensor 100c includes a communicating member 42 which communicates an inside of the fuel tank 20 and an outside of the fuel tank 20 and a connector 40a connected to the communicating member 42. The connector 40a is connected to another device (not illustrated) outside of the fuel tank 20.

Second Embodiment

Figure 15:
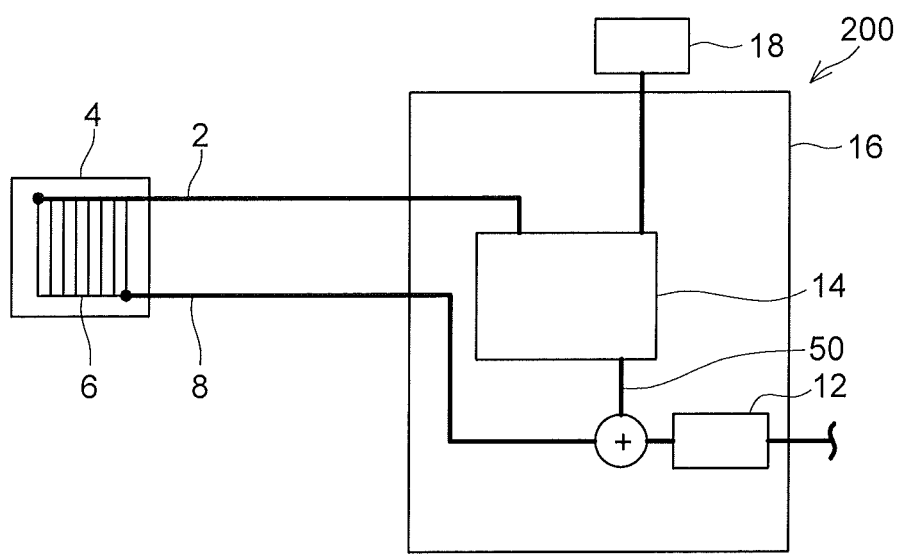
FIG. 15 is a schematic view of a fuel property sensor according to a second embodiment.

A fuel property sensor 200 is described with reference to FIG. 15. The fuel property sensor 200 is a modification of the fuel property sensor 100. The fuel property sensor 200 differs from the fuel property sensor 100 in that a signal outputting unit 14 of the fuel property sensor 200 outputs signals to a plurality of lead wires. Components of the fuel property sensor 200 which are substantially identical to those of the fuel property sensor 100 are given the same reference numerals as those of the fuel property sensor 100, and as such, may not be described below.

In the fuel property sensor 200, the signal output unit 14 outputs signals to the first lead wire 2 and a third lead wire 50. As will be described in detail later, a signal that is outputted to the first lead wire 2 and a signal that is outputted to the third lead wire 50 are different from each other. The third lead wire 50 is connected to the second lead wire 8. Therefore, the signal receiving unit 12 receives a combined wave of the signal from the second lead wire 8 and the signal from the third lead wire 50.

Figure 16:
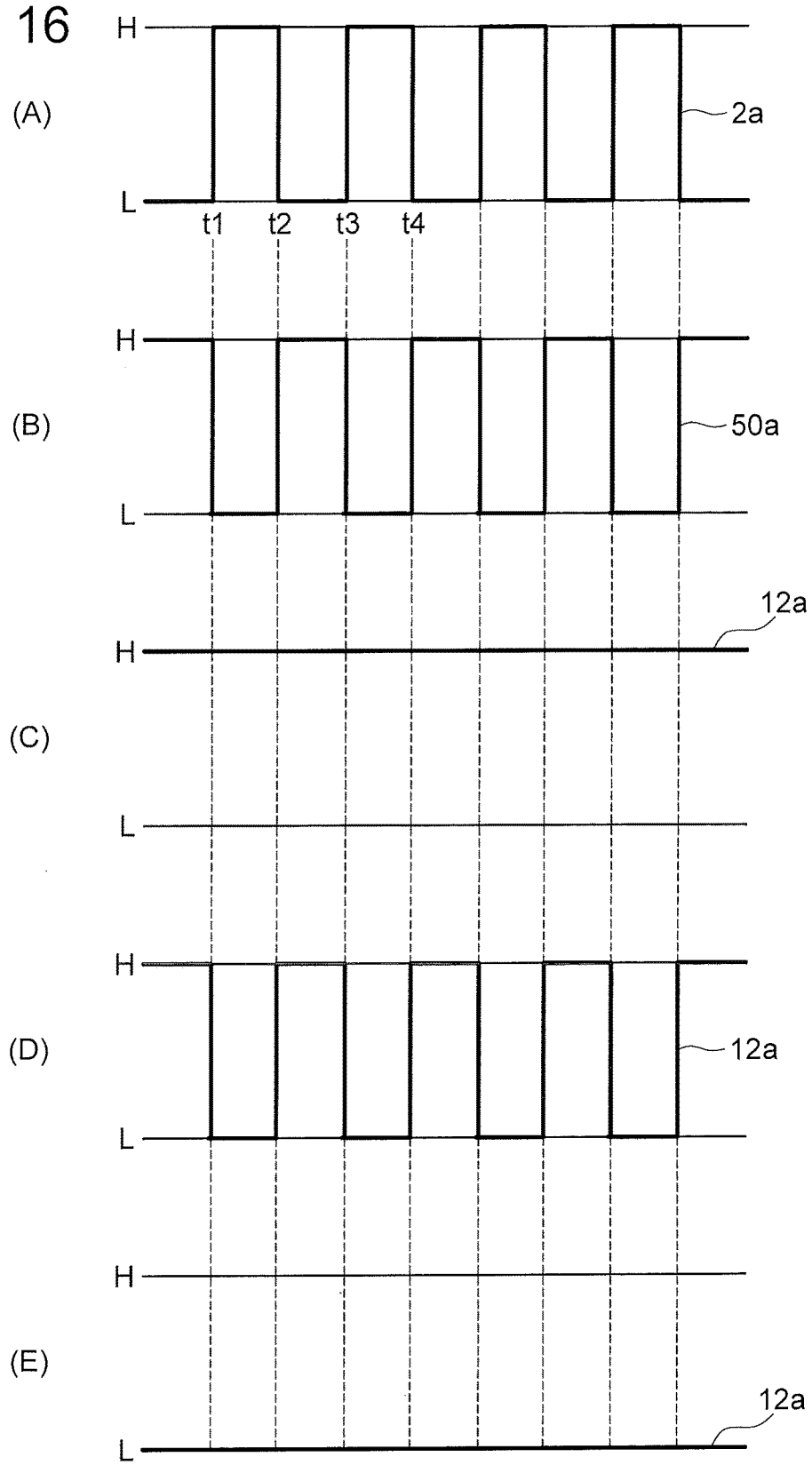
FIG. 16 is a diagram explaining how the fuel property sensor according to the second embodiment operates.

FIG. 16 shows an aspect in which a property of fuel is measured by using the fuel property sensor 200. A waveform (A) shows a signal 2a that is outputted to the first lead wire 2 by the signal outputting unit 14, and a waveform (B) shows a signal 50a that is outputted to the third lead wire 50 by the signal outputting unit 14. As clearly shown in FIG. 16, the signal 2a and the signal 50a are opposite in phase to each other. Waveforms (C) to (E) show a signal 12a that is received by the signal receiving unit 12. The waveform (C) shows a state in which the wiring member 6 connects the first lead wire 2 and the second lead wire 8. A waveform (D) shows a state in which the wiring member 6 disconnects the first lead wire 2 and the second lead wire 8 from each other. A waveform (E) shows a state in which there is a failure in the fuel property sensor 200 per se. As clearly shown in FIG. 16, the waveforms (C) to (E) show different shapes. Use of the fuel property sensor 200 makes it possible to determine presence and absence of a failure in the fuel property sensor 200 per se, in addition to whether sulfur is contained in the fuel.

Figure 17:
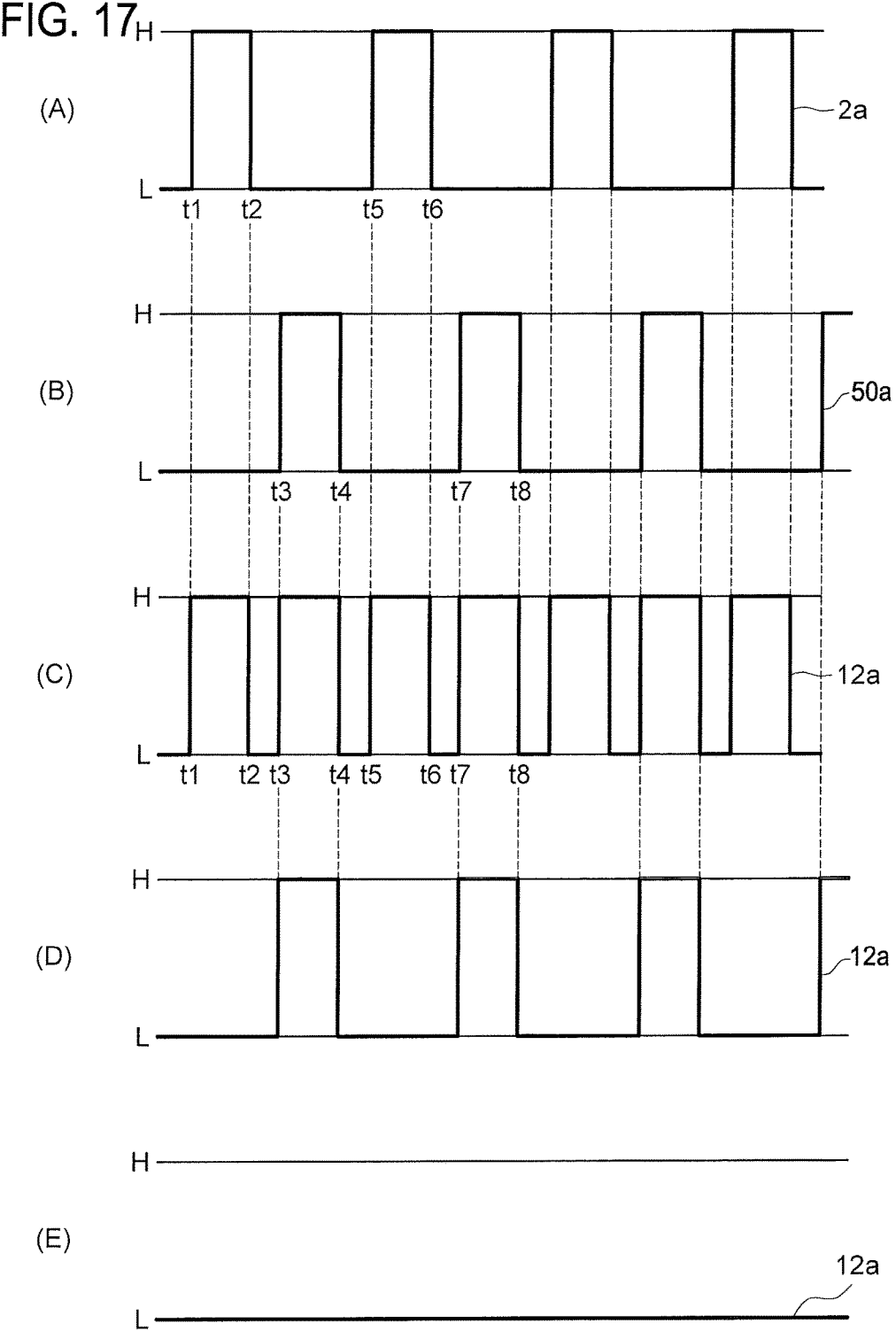
FIG. 17 is a diagram explaining how the fuel property sensor according to the second embodiment operates.

FIG. 17 shows another aspect in which a property of fuel is measured by using the fuel property sensor 200. A waveform (A) shows a signal 2a that is outputted to the first lead wire 2 by the signal outputting unit 14, and a waveform (B) shows a signal 50a that is outputted to the third lead wire 50 by the signal outputting unit 14. Waveforms (C) to (E) show a signal 12a that is received by the signal receiving unit 12. The signal 2a and the signal 50a are out of phase with each other. The signal 2a rises to a High state at a timing t1, falls to a Low state at a timing t2, rises to the High state at a timing t5, and falls to the Low state at a timing t6. The signal 2a repeats such changes in state. Further, in a period between the timing t2 and the timing t5, the signal 50a rises to a High state at a timing t3 and falls to a Low state at a timing t4. After the timing t6, the signal 50a repeats similar changes in state (see timings t7 and t8).

The signal 12a shows the waveform (C) when the wiring member 6 connects the first lead wire 2 and the second lead wire 8, the waveform (D) when the wiring member 6 disconnects the first lead wire 2 and the second lead wire 8 from each other, and the waveform (E) when there is a failure in the fuel property sensor 200 per se. Also when the signal 2a and the signal 50a are outputted out of phase with each other, it is possible to determine presence or absence of a failure in the fuel property sensor 200 per se, in addition to whether sulfur is contained in the fuel.

Figure 18:
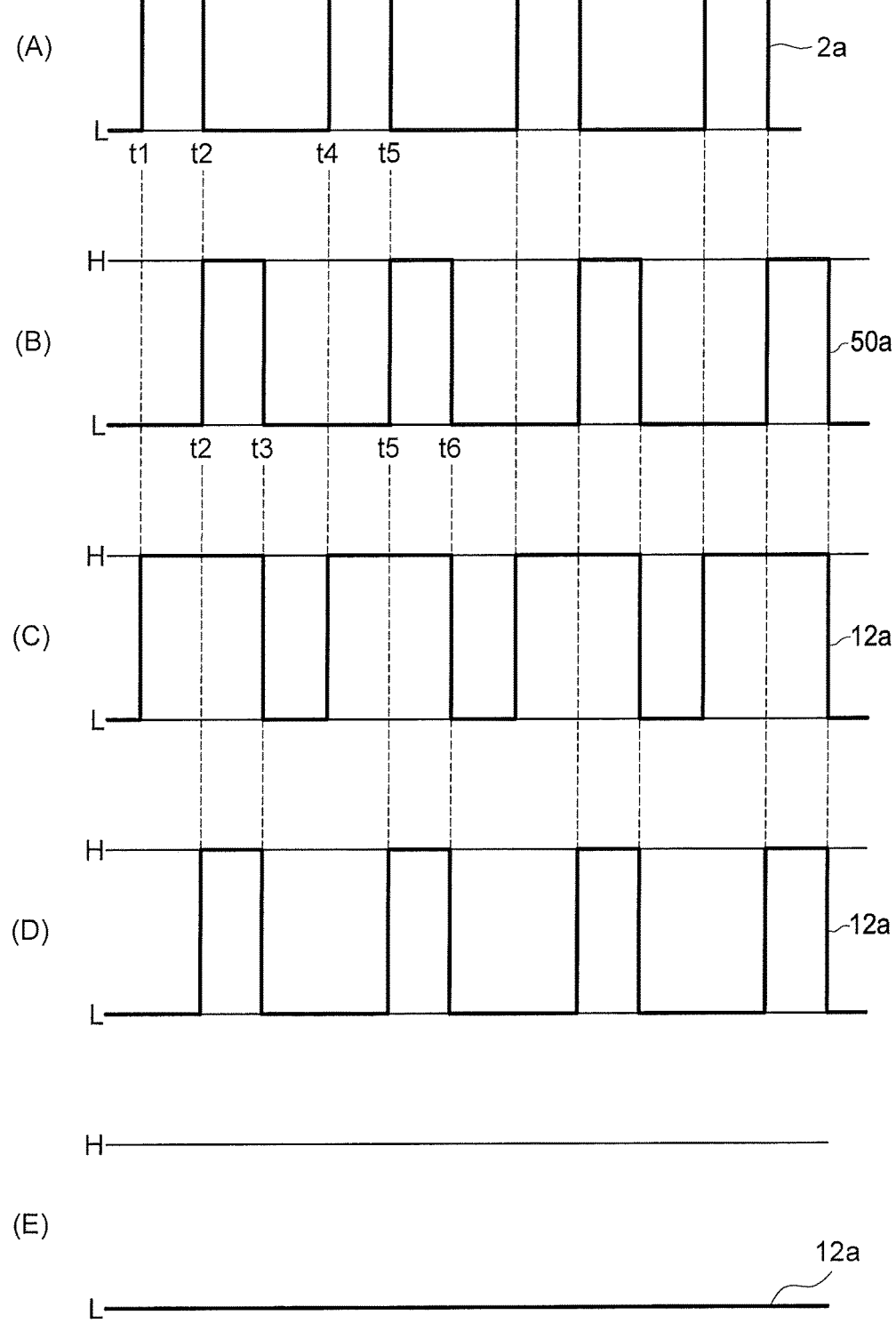
FIG. 18 is a diagram explaining how the fuel property sensor according to the second embodiment operates.

FIG. 18 shows another aspect in which a property of fuel is measured by using the fuel property sensor 200. A waveform (A) shows a signal 2a that is outputted to the first lead wire 2 by the signal outputting unit 14, and a waveform (B) shows a signal 50a that is outputted to the third lead wire 50 by the signal outputting unit 14. Waveforms (C) to (E) show a signal 12a that is received by the signal receiving unit 12. The signal 2a and the signal 50a are out of phase with each other. The signal 2a rises to a High state at a tuning t1, falls to a Low state at a timing t2, rises to the High state at a timing t4, and falls to the Low state at a timing t5. The signal 2a repeats such changes in state. The signal 50a rises to a High state at the timing t2 and falls to a Low state at a timing t3 between the tuning t2 and the timing t4. Further, the signal 50a rises to the High state at the timing t5, and repeats similar changes in state afterward.

As just described, the signal 2a falls to the Low state and the signal 50a rises to the High state at the same timings (timings t2 and t5). Therefore, the signal 12a shows the waveform (C) when the wiring member 6 connects the first lead wire 2 and the second lead wire 8, the waveform (D) when the wiring member 6 disconnects the first lead wire 2 and the second lead wire 8 from each other, and the waveform (E) when there is a failure in the fuel property sensor 200 per se. Also when the signal 2a and the signal 50a are thus outputted out of phase with each other, it is possible to determine presence or absence of a failure in the fuel property sensor 200 per se, in addition to whether sulfur is contained in the fuel.

Third Embodiment

Figure 19:
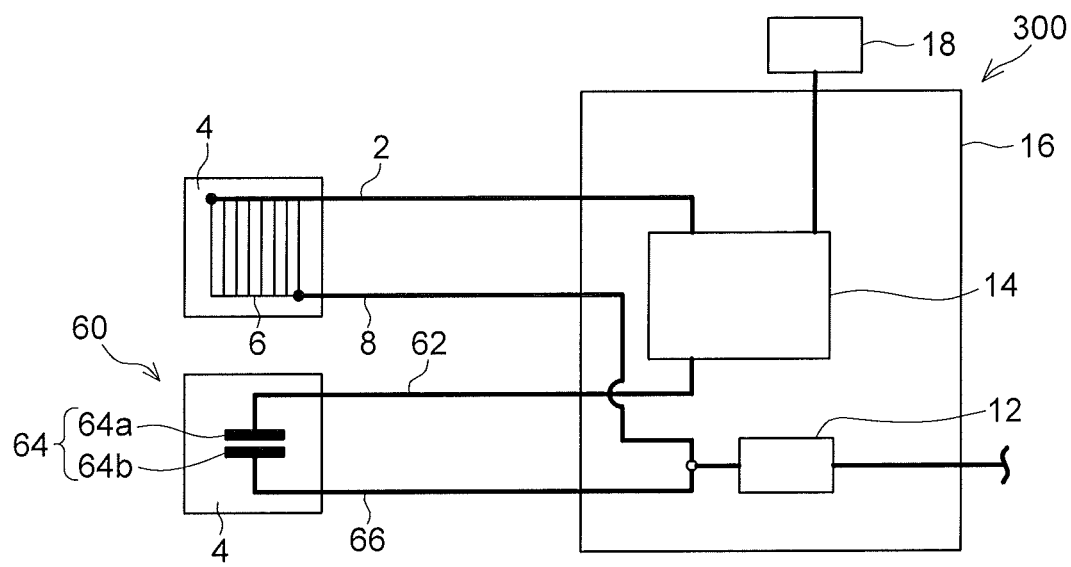
FIG. 19 is a schematic view of a fuel property sensor according to a third embodiment.

A fuel property sensor 300 is described with reference to FIG. 19. The fuel property sensor 300 is a modification of the fuel property sensors 100 and 200. The fuel property sensor 300 differs from the fuel property sensors 100 and 200 in that the fuel property sensor 300 includes a water detector 60. Components of the fuel property sensor 300 which are substantially identical to those of the fuel property sensors 100 and 200 are given the same reference numerals as those of the fuel property sensors 100 and 200, and as such, may not be described below.

The water detector 60 includes an electrode pair 64. The electrode pair 64 is provided on the front surface of the substrate 4. The electrode pair 64 includes a first electrode 64a and a second electrode 64b spaced from the first electrode 64a. A third lead wire 62 is connected to the first electrode 64a, and a fourth lead wire 66 is connected to the second electrode 64b. The third lead wire 62 is connected to the signal outputting unit 14. The fourth lead wire 66 is connected to the signal receiving unit 12. Further, the fourth lead wire 66 is connected to the second lead wire 8. That is, the second electrode 64b is connected to the second lead wire 8. It should be noted that although it appears in FIG. 19 that the substrate 4 on which the wiring member 6 is provided and the substrate 4 on which the electrode pair 64 is provided are separate, the wiring member 6 and the electrode pair 64 are actually provided on the same substrate 4.

Since the first electrode 64a and the second electrode 64b are out of contact with each other, the third lead wire 62 and the fourth lead wire 66 are electrically disconnected from each other in the absence of water around the electrode pair 64. On the other hand, in the presence of water around the electrode pair 64, the first electrode 64a and the second electrode 64b are short-circuited, whereby the third lead wire 62 and the fourth lead wire 66 are electrically connected to each other. The water detector 60 is configured to detect the presence or absence of water in accordance with whether the third lead wire 62 and the fourth lead wire 66 are electrically connected.

Figure 20:
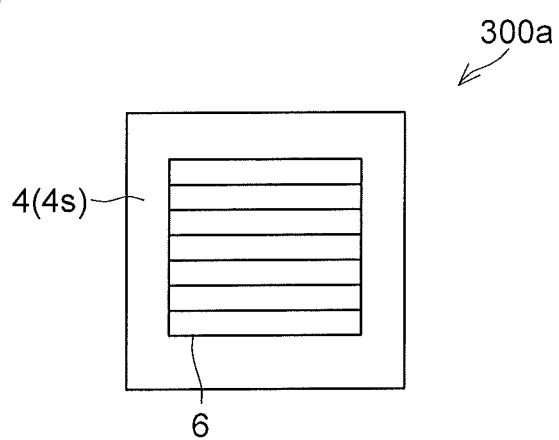
FIG. 20 is a diagram explaining places in which a wiring member and a water detector are disposed.
Figure 21:
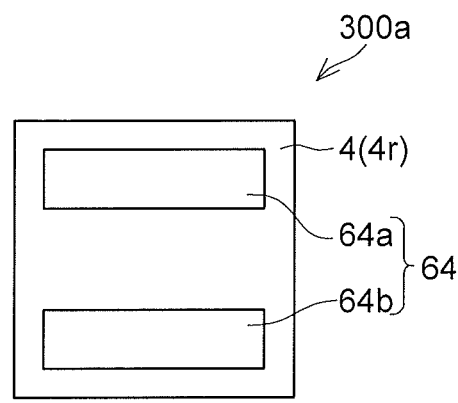
FIG. 21 is a diagram explaining places in which a wiring member and a water detector are disposed.
Figure 22:
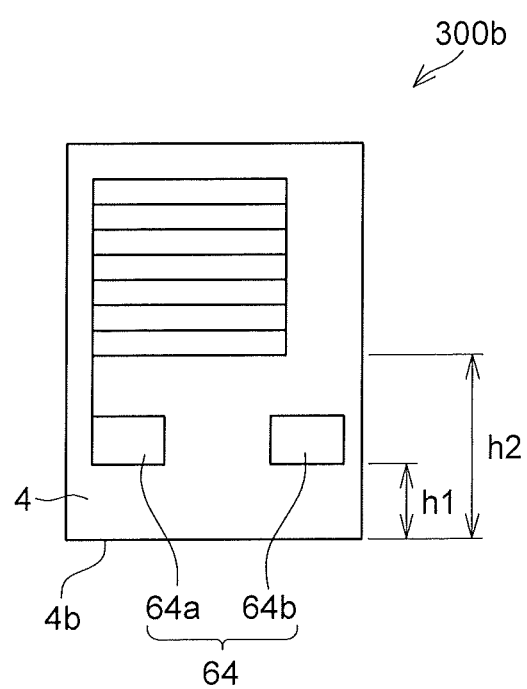
FIG. 22 is a diagram explaining places in which a wiring member and a water detector are disposed.

Examples of places in which the wiring member 6 and the water detector 64 are disposed are explained here with reference to FIGS. 20 to 22. It should be noted that the following explanation refers only to the substrate 4, the wiring member 6 and the water detector 60 (i.e. the first electrode 64a and the second electrode 64b), and omits to illustrate the lead wires and the like, for example.

FIGS. 20 and 21 schematically show a fuel property sensor 300a. In the fuel property sensor 300a, the wiring member 6 and the electrode pair 64 are disposed by using front and rear surfaces of the substrate 4. The wiring member 6 is disposed on the front surface 4s of the substrate 4, and the electrode pair 64 is disposed on the rear surface 4r of the substrate 4. The fuel property sensor 300a enables efficient use of the front and rear surfaces of the substrate 4. It should be noted that water, which is higher in specific gravity than the fuel (gasoline), can be efficiently detected by disposing the fuel property sensor 300a in the fuel tank 20 so that the rear surface 4r faces the bottom face 20a of the fuel tank 20.

FIG. 22 schematically shows a fuel property sensor 300b. In the fuel property sensor 300b, the wiring member 6 and the water detector 64 are both disposed by using one surface of the substrate 4. The fuel property sensor 300b is disposed so that an end face 4b of the substrate 4 faces the bottom face 20a of the fuel tank 20. By appropriately adjusting a distance h1 from the end face 4b to the water detector 64 and a distance h2 from the end face 4b to the wiring member 6, the fuel property sensor 300b can be adjusted so that the water detector 64 functions when water having accumulated in the fuel tank 20 reaches a predetermined value. Further, the fuel property sensor 300b can be adjusted so that the wiring member 6 makes contact with the fuel, without being surrounded by water.

How the fuel property sensor 300 operates is described with reference to FIGS. 23 to 26. Each waveform (A) shows a signal 2a that is outputted to the first lead wire 2 by the signal outputting unit 14. Each waveform (B) shows a signal 8a that is outputted from the wiring member 6 to the second lead wire 8. Each waveform (C) shows a signal 62a that is outputted to the third lead wire 62 by the signal outputting unit 14. Each waveform (D) shows a signal 66a that is outputted from the second electrode 64b to the fourth lead wire 66. Each waveform (E) shows a signal 12a (i.e. a combined wave of the signal 8a and the signal 66a) that is received by the signal receiving unit 12. It should be noted that the signal 2a and the signal 62a are opposite in phase to each other.

FIG. 23 shows a state in which the first lead wire 2 and the second lead wire 8 are electrically connected to each other and the first electrode 64a and the second electrode 64b are electrically disconnected from each other. That is, FIG. 23 shows a state in which the fuel is of good quality and no water has accumulated in the fuel tank 20. The waveform of the signal 8a is identical to the waveform of the signal 2a. The signal 66a is always in a Low state. Therefore, the waveform of the signal 12a is identical to the waveform of the signal 2a.

FIG. 24 shows a state in which the first lead wire 2 and the second lead wire 8 are electrically disconnected from each other and the first electrode 64a and the second electrode 64b are electrically disconnected from each other. That is, FIG. 24 shows a state in which impurities are contained in the fuel and no water has accumulated in the fuel tank 20. The signal 8a and the signal 66a are always in a Low state. Therefore, the signal 12 is always in the Low state, too.

Figure 25:
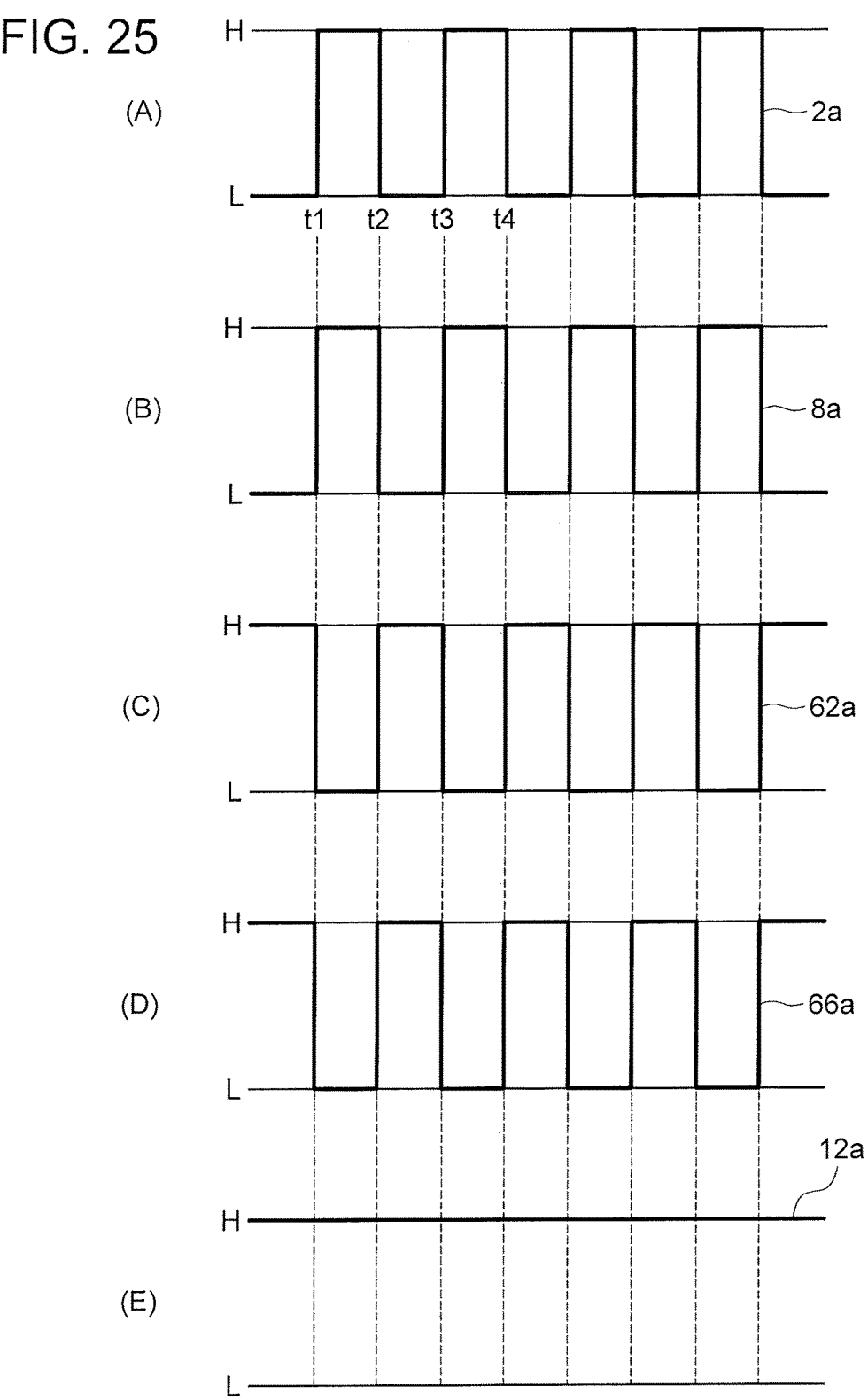
FIG. 25 is a diagram explaining how the fuel property sensor according to the third embodiment operates.

FIG. 25 shows a state in which the first lead wire 2 and the second lead wire 8 are electrically connected to each other and the first electrode 64a and the second electrode 64b are electrically connected to each other. That is, FIG. 25 shows a state in which the fuel is of good quality and water has accumulated in the fuel tank 20. The waveform of the signal 8a is identical to the waveform of the signal 2a. Further, the waveform of the signal 66a is identical to the waveform of the signal 62a. Since the signal 2a and the signal 62a are opposite in phase to each other, the signal 12a is always in a High state, too.

Figure 26:
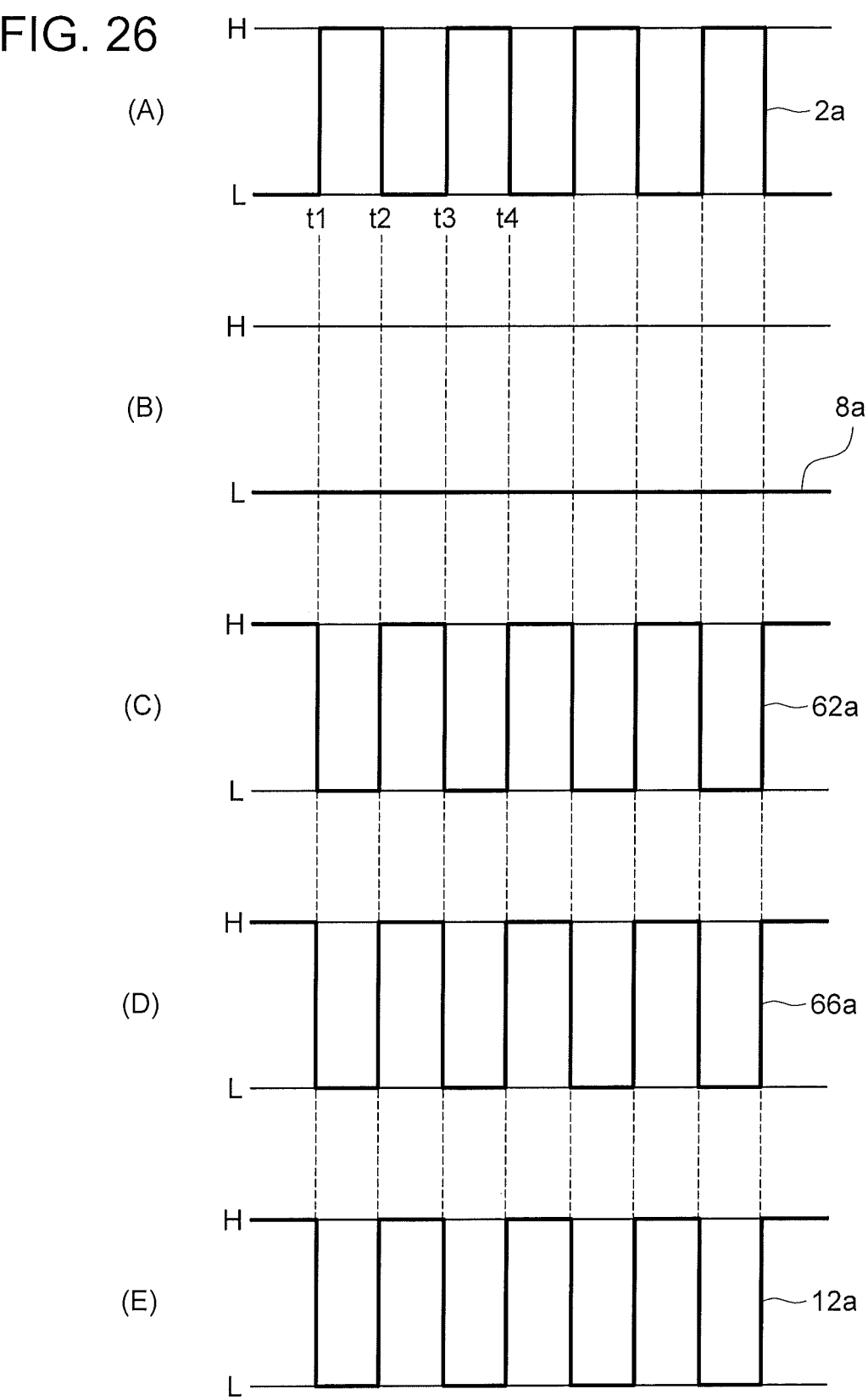
FIG. 26 is a diagram explaining how the fuel property sensor according to the third embodiment operates.

FIG. 26 shows a state in which the first lead wire 2 and the second lead wire 8 are electrically disconnected from each other and the first electrode 64a and the second electrode 64b are electrically connected to each other. That is, FIG. 26 shows a state in which impurities are contained in the fuel and water has accumulated in the fuel tank 20. The signal 8a is always in a Low state. Further, the waveform of the signal 66a is identical to the waveform of the signal 62a. Therefore, the waveform of the signal 12a is identical to the waveform of the signal 62a.

As described above, the fuel property sensor 300 can detect independently each of whether impurities are contained in the fuel and whether water has accumulated in the fuel tank 20. In the fuel property sensor 300, the signal outputting unit 14 outputs, to the first lead wire 2 and the third lead wire 62, signals that are opposite in phase to each other (i.e. the signals 2a and 62a). Alternatively, the signal outputting unit 14 may output, to the first lead wire 2 and the third lead wire 62, signals that are out of phase with each other, as in the case of the fuel property sensor 200 where the signals 2a and 50a, which are out of phase with each other, are outputted, to the first lead wire 2 and the third lead wire 50 (see also FIGS. 17 and 18).

Fourth Embodiment

Figure 27:
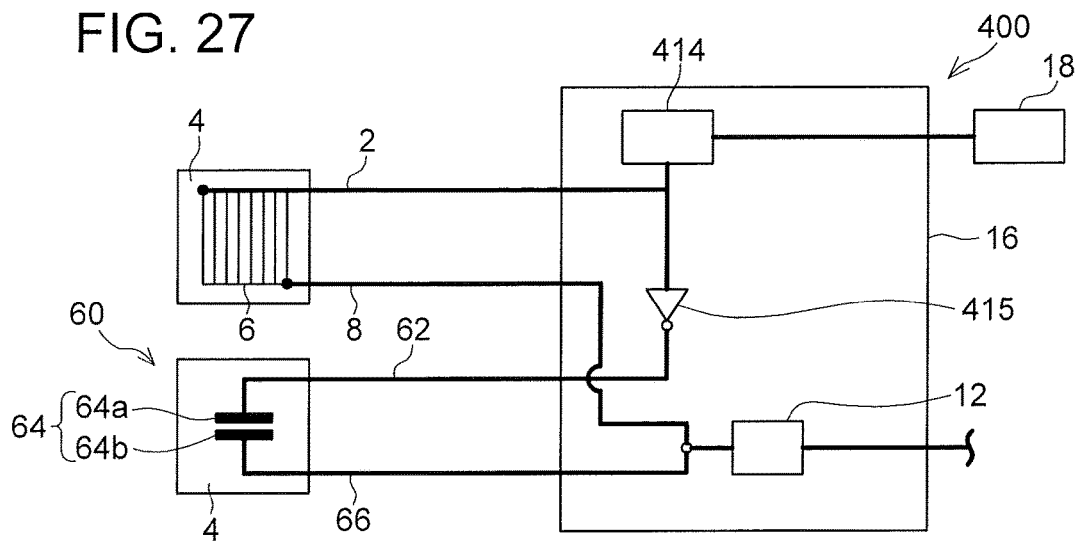
FIG. 27 is a schematic view of a fuel property sensor according to a fourth embodiment.

A fuel property sensor 400 is described with reference to FIG. 27. The fuel property sensor 400 is a modification of the fuel property sensor 300. The fuel property sensor 400 differs from the fuel property sensor 300 in that the fuel property sensor 400 includes a signal outputting unit 414 configured to output signals that are different from the signals that are outputted from the signal outputting unit 14 of the fuel property sensor 300. Components of the fuel property sensor 400 which are substantially identical to those of the fuel property sensor 300 are given the same reference numerals or reference numerals with the same lower two digits as those of the fuel property sensor 300, and as such, may not be described below.

The signal outputting unit 414 outputs a same signal to the first lead wire 2 and the third lead wire 62. However, an inverter 415 is disposed between the signal outputting unit 414 and the third lead wire 62 to invert the signal outputted from the signal outputting unit 414. Therefore, the signal that is supplied to the wiring member 6 and the signal that is supplied to the first electrode 64a are opposite in phase to each other. As with the fuel property sensor 300, the fuel property sensor 400 can detect independently each of whether impurities are contained in the fuel and whether water has accumulated in the fuel tank 20. The fuel property sensor 400 allows the signal outputting unit 414 to output fewer signals than the counterpart of the fuel property sensor 300.

Fifth Embodiment

Figure 28:
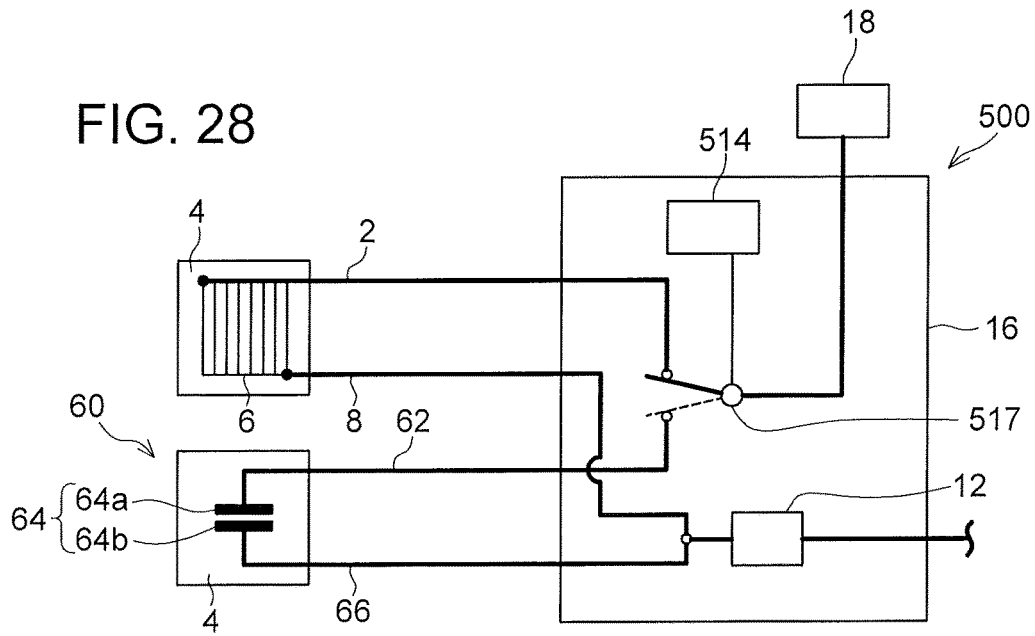
FIG. 28 is a schematic view of a fuel property sensor according to a fifth embodiment.

A fuel property sensor 500 is described with reference to FIG. 28. The fuel property sensor 500 is a modification of the fuel property sensor 300. The fuel property sensor 500 differs from the fuel property sensor 300 in that the fuel property sensor 500 includes a signal outputting unit 514 configured to output signals that are different from the signals that are outputted from the signal outputting unit 14 of the fuel property sensor 300. Components of the fuel property sensor 500 which are substantially identical to those of the fuel property sensor 300 are given the same reference numerals or reference numerals with the same lower two digits as those of the fuel property sensor 300, and as such, may not be described below.

The signal outputting unit 514 outputs, to a switch 517, a signal that is always in a High state. The switch 517 is connected alternately to the first lead wire 2 and the third lead wire 62 at regular intervals. The signal that is outputted from the signal outputting unit 514 is inputted alternately to the first lead wire 2 and the third lead wire 62. Therefore, the signal that is supplied to the wiring member 6 and the signal that is supplied to the first electrode 64a are opposite in phase to each other. As with the fuel property sensors 300 and 400, the fuel property sensor 500 can detect independently each of whether impurities are contained in the fuel and whether water has accumulated in the fuel tank 20. Further, the fuel property sensor 500 allows the signal outputting unit 514 to output fewer signals than the counterpart of the fuel property sensor 300.

Each of the above embodiments has been described by taking, as an example, a case where the signal outputting units are configured to output digital signals. The signal outputting units may be configured to output analog signals. In that case, a signal that is inputted to the signal receiving unit may be binarized by using a particular threshold value. Further, each of the fuel property sensors 300, 400, and 500 has been described by taking, as an example, a case where different signals are supplied to the wiring member 6 and the water detector 60 (first electrode 64a). Alternatively, the signal outputting unit may be connected to the wiring member 6 and the water detector 60 (first electrode 64a) via a common lead wire.

Specific examples of the present invention are described above in detail, but these examples are merely illustrative and place no limitation on the scope of the patent claims. The technology described in the patent claims also encompasses various changes and modifications to the specific examples described above. The technical elements explained in the present specification or drawings provide technical utility either independently or through various combinations. The present invention is not limited to the combinations described at the time the claims are filed. Further, the purpose of the examples shown by the present specification or drawings is to satisfy multiple objectives simultaneously, and satisfying any one of those objectives gives technical utility to the present invention.

What is claimed is:

1. A fuel property sensor for detecting a property of fuel used in an engine, the sensor comprising:
   a substrate configured to be disposed in such a position as to be in contact with the fuel;
   a first lead wire connected to the substrate;

a second lead wire connected to the substrate and spaced from the first lead wire;

a wiring member provided on the substrate, connecting the first lead wire and the second lead wire, and configured to electrically disconnect the first lead wire and the second lead wire from each other by reaction with impurities contained in the fuel;

a determiner configured to determine whether the first lead wire and the second lead wire are electrically connected; and a water detector configured to detect water in the fuel, wherein the determiner comprises a signal outputting unit configured to output a first signal to the first lead wire and a signal receiving unit configured to receive a second signal from the second lead wire, the determiner is configured to determine, in accordance with the first signal and the second signal, whether the first lead wire and the second lead wire are electrically connected, the water detector comprises a first electrode connected to the signal outputting unit and a second electrode connected to the signal receiving unit, the second electrode being spaced from the first electrode, the water detector is configured to detect a presence or absence of water in accordance with whether the first electrode and the second electrode are electrically connected, and the second electrode is connected to the second lead wire.

2. The fuel property sensor according to claim 1, wherein the wiring member has a film shape.

3. The fuel property sensor according to claim 1, wherein the wiring member is configured of a conductive material adhering on the substrate.

4. The fuel property sensor according to claim 3, wherein the wiring member is configured of conductive ink applied on the substrate.

5. The fuel property sensor according to claim 3, wherein the wiring member is configured of a plated predetermined portion of the substrate.

6. The fuel property sensor according to claim 1, wherein non-wiring regions are provided in a repetitive arrangement between the first lead wire and the second lead wire, and the wiring member is not provided in any of the non-wiring regions.

7. The fuel property sensor according to claim 1, wherein the water detector is disposed on the substrate.

* * * * *